United States Patent [19]

Hauck et al.

[11] 4,350,812
[45] Sep. 21, 1982

[54] ANTIARRHYTHMIC TETRAHYDRONAPHTHALENE DERIVATIVES

[75] Inventors: Frederic P. Hauck, Bridgewater; Rita T. Fox, Princeton, both of N.J.

[73] Assignee: E. R. Squibb & Sons, Inc., Princeton, N.J.

[21] Appl. No.: 290,558

[22] Filed: Aug. 6, 1981

Related U.S. Application Data

[60] Division of Ser. No. 195,685, Oct. 9, 1980, Pat. No. 4,302,453, which is a continuation-in-part of Ser. No. 93,654, Nov. 13, 1979, abandoned.

[51] Int. Cl.³ .............. C07C 103/29; C07C 103/85; C07D 265/30
[52] U.S. Cl. .............. 544/79; 260/239 BC; 260/239 BF; 260/245.7; 260/330; 544/58.4; 544/357; 546/187; 546/189; 548/200; 548/215; 548/300; 548/518; 564/156; 549/433
[58] Field of Search .............. 260/239 BF, 239 BC, 260/245.7, 326.25, 330, 333; 544/58.4, 79, 357; 546/187, 189; 548/200, 215, 300; 564/156

[56] References Cited

PUBLICATIONS

Condon et al., J. Med. Soc., vol. 21 (1978), pp. 913–922.

*Primary Examiner*—Richard Raymond
*Attorney, Agent, or Firm*—Lawrence S. Levinson; Burton Rodney

[57] ABSTRACT

Compounds are provided having the structure

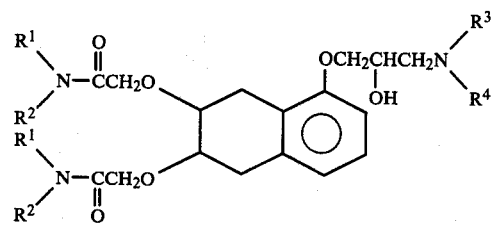

wherein $R^1$ and $R^2$ may be the same or different and are hydrogen, lower alkyl, lower alkenyl, or hydroxylower alkyl, or $R^1$ and $R^2$ together with the nitrogen atom to which they are attached also form a heterocyclic radical which may contain another heteroatom, namely nitrogen, oxygen or sulfur; $R^3$ and $R^4$ may be the same or different and are hydrogen or lower alkyl. These compounds are useful in the treatment of arrhythmia.

In addition, novel intermediates are provided having the structure

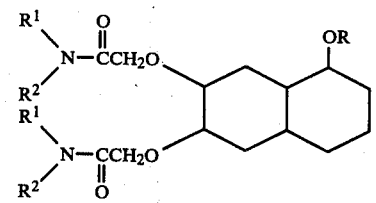

wherein R is hydrogen, benzyl or

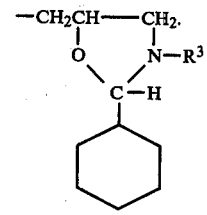

These intermediates are also useful in treating acute myocardial infarction.

8 Claims, No Drawings

ANTIARRHYTHMIC TETRAHYDRONAPHTHALENE DERIVATIVES

REFERENCE TO OTHER APPLICATIONS

This is a division of application Ser. No. 195,685, filed Oct. 9, 1980, now U.S. Pat. No. 4,302,453 which is a continuation-in-part of application Ser. No. 93,654, filed Nov. 13, 1979, now abandoned.

DESCRIPTION OF THE INVENTION

The present invention relates to compounds having the structure

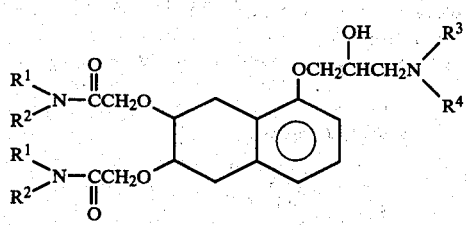

wherein $R^1$ and $R^2$ may be the same or different and can be hydrogen, lower alkyl, lower alkenyl or hydroxy-lower alkyl, or $R^1$ and $R^2$ may be taken together with the nitrogen atom to which they are attached to form a heterocyclic radical which may contain in addition to such nitrogen atom, one other heteroatom which can be nitrogen, oxygen or sulfur; and $R^3$ and $R^4$ may be the same or different and can be hydrogen or lower alkyl, and acid-addition salts and stereoisomers thereof.

The term "lower alkyl" as employed herein includes both straight and branched chain radicals of up to 8 carbons, preferably 1 to 4 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl and the like as well as such groups including a halo-substituent, such as F, Br, Cl or I or $CF_3$ or a phenyl substituent.

The term "lower alkenyl" as employed herein includes an unsaturated hydrocarbon group having from 3 to 8 carbons and a single carbon-carbon double bond, such as ethenyl, 1-propenyl, 2-propenyl, 1-butenyl, 2-butenyl, 3-butenyl and the like.

As indicated, the group

may form a heterocyclic radical containing in addition to nitrogen, one other heteroatom, such as nitrogen, oxygen or sulfur, and may contain up to 5 carbons.

Illustrative of the heterocyclic radicals represented by

are the following: piperidino; (lower alkyl)piperidino [e.g., 2-,3-, or 4-(lower alkyl)piperidino, such as 2-(ethyl)piperidino]or di(lower alkyl)piperidino [e.g., 2,4-, 2,5- or 3,5-di(lower alkyl)piperidino such as 2,4-dimethylpiperidino or 2,5-di-t-butyl piperidino]; (lower alkoxy)piperidino [e.g., 2-methoxypiperidino or 3-methoxypiperidino]; hydroxypiperidino [e.g., 3-hydroxy- or 4-hydroxypiperidino]; aminomethyl-piperidino [e.g., 4-aminomethylpiperidino]; pyrrolidino; (lower alkyl)pyrrolidino [e.g., 3-methylpyrrolidino]; di(lower alkyl)pyrrolidino [e.g., 3,4-dimethylpyrrolidino]; (lower alkoxy)pyrrolidino [e.g., 2-methoxypyrrolidino]; morpholino; (lower alkyl)morpholino [e.g., 3-methylmorpholino]; di(lower alkyl)morpholino [e.g., 3,5-dimethylmorpholino]; (lower alkoxy)morpholino [e.g., 2-methoxymorpholino]; thiamorpholino; (lower alkyl)thiamorpholino [e.g., 3-methylthiamorpholino]; di(lower alkyl) thiamorpholino [e.g., 3,5-dimethylthiamorpholino]; (lower alkoxy)thiamorpholino [e.g., 3-methoxythiamorpholino]; piperazino; (lower alkyl)piperazino [e.g., $N^4$-methylpiperazino]; di(lower alkyl)piperazino [e.g., 2,5-dimethylpiperazino or 2,6-dimethylpiperazino]; (lower alkoxy)piperazino [e.g., 2-methoxypiperazino]; (hydroxy-lower alkyl)-piperazino [e.g., $N^4$-(2-hydroxyethyl)piperazindo]; (alkanoyloxy-lower alkyl)piperazino wherein the alkanoyloxy group has up to 14 carbons [e.g., $N^4$-(2-heptanoyloxyethyl)piperazino or $N^4$-(2-dodecanoyloxyethyl)piperazino]; (hydroxy-lower alkoxy-lower alkyl)-piperazino [e.g., (hydroxymethoxy-methyl)piperazino]; (carbo-lower alkoxy)piperazino [e.g., $N^4$-(carbomethoxy-, carboethoxy-, or carbopropoxy)piperazino]; homopiperazino; or $N^4$-(hydroxy-lower alkyl)-homopiperazino [e.g., $N^4$-(2-hydroxyethyl)-homopiperazino].

The compounds of formula I form acid-addition salts by reaction with various inorganic and organic acids. These salts frequently provide convenient means for separating the product from the reaction mixture in which it is produced or from the solvent in which it is extracted in view of their insolubility in various media. Thus the product may be precipitated in the form of an insoluble salt and converted, by conventional techniques, to the free base or to another soluble or insoluble salt as desired.

Illustrative salts include the hydrohalides, such as hydrochloride, hydrobromide and hydroiodide, especially the first two, other mineral acid salts, such as phosphate, sulfate, nitrate, etc., organic acid salts, such as oxalate, tartrate, malate, maleate, citrate, pamoate, fumarate, camphosulfonate, methanesulfonate, benzenesulfonate, toluenesulfonate, salicylate, benzoate, ascorbate, mandelate, or the like.

The compounds of formula I also form quaternary ammonium salts with lower alkyl halides, for example, methyl bromide, ethyl bromide and propyl iodide; benzyl halides, such as benzyl chloride; and dilower alkyl sulfates, such as dimethyl sulfate. To form the quaternary ammonium salts, the free base initially formed is intereacted with at least one equivalent of the desired alkylating agent.

Preferred are those compounds of formula I wherein $R^1$ and $R^2$ are each n-propyl or

taken together is morpholinyl, and $R^3$ and $R^4$ are hydrogen or one of $R^3$ and $R^4$ is t-butyl.

The compounds of formula I of the invention include all stereoisomers and mixtures thereof. Thus, either of the acetamidyloxy groups may be cis or trans to the aminohydroxypropyloxy chain.

The most preferred compound of the invention is in the cis form of 2,2'-[[5-[3-[(1,1-dimethylethyl)amino]-2-hydroxypropoxy]-1,2,3,4-tetrahydro-2,3-naphthalenediyl]bis (oxy)]bis[N,N-dipropylacetamide]. This compound has three assymetric centers and thus include the following isomers:

A. [2S-[2α,3α,5(S*)]]-2,2'-[[5-[3-[(1,1-Dimethylethyl)amino]-2-hydroxypropoxy]-1,2,3,4-tetrahydro-2,3-naphthalenediyl]bis(oxy)]bis[N,N-dipropylacetamide]

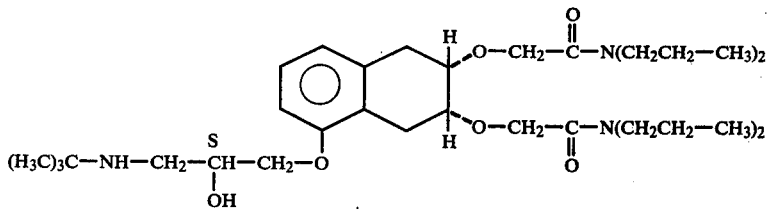

B. [2R-[2α,3α,5(R*)]]-2,2'-[[5-[3-[(1,1-Dimethylethyl)amino]-2-hydroxypropoxy]-1,2,3,4-tetrahydro-2,3-naphthalenediyl]bis(oxy)]bis[N,N-dipropylacetamide]

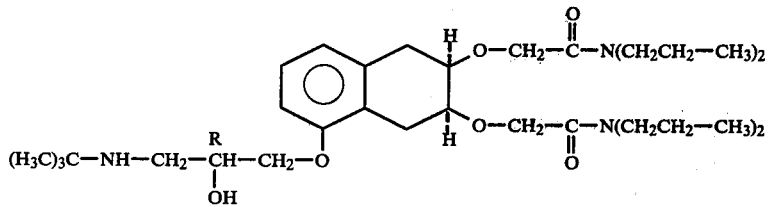

C. [2R-[2α,3α,5(S*)]]-2,2'-[[5-[3-[(1,1-Dimethylethyl)amino]-2-hydroxypropoxy]-1,2,3,4-tetrahydro-2,3-naphthalenediyl]bis(oxy)]bis[N,N-dipropylacetamide]

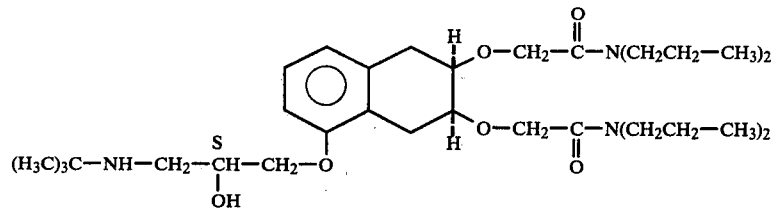

D. [2S-[2α, 3α,5(R*)]]-2,2'-[[5-[3-[(1,1-Dimethylethyl)amino]-2-hydroxypropoxy]-1,2,3,4-tetrahydro-2,3-naphthalenediyl]bis(oxy)]bis[N,N-dipropylacetamide]

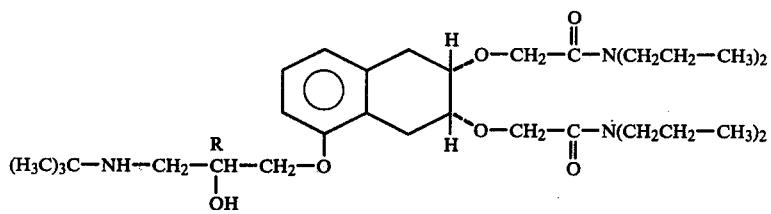

It has been found that one of the above optically active isomers A, B, C and D is substantially superior to the others in treating arrhythmia while, surprisingly, at the same time, is substantially less toxic than the others. The superior, but less toxic, antiarrhythmia agent of the invention is the optically active isomer B, namely, B. [2R-[2α,3α,5(R*)]]-2,2'-[[5-[3-[(1,1-Dimethylethyl)amino]-2-hydroxypropoxy]-1,2,3,4-tetrahydro-2,3-naphthalenediyl]bis(oxy)]bis[N,N-dipropylacetamide] which has the structure

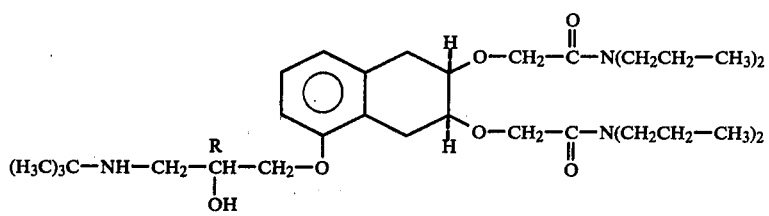

The isomer B may be prepared as described in application Ser. No. 195,684 now U.S. Pat. No. 4,326,076—Apr. 20, 1982 (Moniot) filed concurrently herewith.

The compounds of formula I may be formed by reacting 1,2,3,4-tetrahydro-5-(phenylmethoxy)-2,3-naphthalenediol

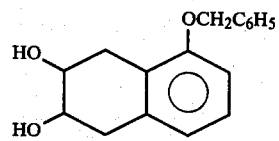

II with a haloacetamide III

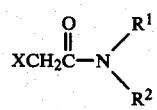

III wherein X is Cl or Br to form a 2,2'-[1,2,3,4-tetrahydro-5-(phenylmethoxy)-[2,3-naphthalenediyl]bis(oxy)]bis[-substituted acetamide] of the structure

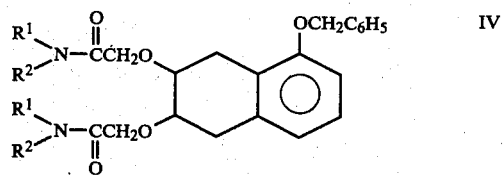

IV

The formula IV compounds represent a new class of intermediates and also show activity against acute myocardial infraction as indicated by the test described by Harris, A. S. "Delayed Development of Ventricular Ectopic Rhythms Following Experimental Coronary Occlusion", Circulation 1:1318–1328, 1950.

The above reaction is carried out employing a molar ratio of II:III of within the range of from about 1:2 to about 1:4 in the presence of a base, such as sodium hydride or sodamide in a solvent, such as dimethyl sulfoxide, tetrahydrofuran, dimethylformamide or dioxane, while maintaining the temperature of the reaction mixture of within the range of from about 0° to about 50° C. for periods of from 5 to 72 hours.

The formula IV benzyloxy compound is then reduced to the corresponding hydroxy derivatives by hydrogenating same in the presence of a hydrogenation catalyst, such as palladium on carbon, or platinum oxide in the presence of a lower alkanol solvent, such as ethanol to form the formula V hydroxy compound

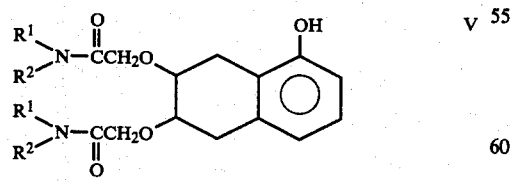

V

The formula V compound is also a novel intermediate and has been found to be active against acute myocardial infarction.

The formula V compound is converted to the correspoding epoxy derivative VI by reacting V with epichlorohydrin in an inert solvent, such as acetone, dioxane, tetrahydrofuran and water containing sodium hydroxide to form the epoxide VII

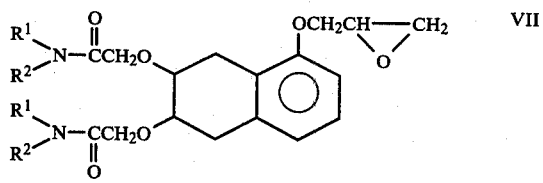

VII

The above reaction is carried out preferably at reflux temperature of the solvent while stirring vigorously for periods of from 0.5 to 7 hours.

Alternatively, the reaction may be carried out in anhydrous dimethylsulfoxide or dimethylformamide using sodium methoxide as the condensing agent, at a temperature of 5° to 30° C. for 3 to 20 hours.

Alternatively, VII is prepared by alkylation of epoxydiol XV (cis or trans—J. Med. Chem. 21, 913 (1978) with haloacetamide as described in the conversion of II to IV.

The epoxide VII is converted to the formula I compounds of the invention by reacting VII with an amine

VIII in a molar ratio of VII:VIII of within the range of from about 1:1 to about 1:10 in the presence of a lower alkanol, such as methanol or ethanol, for periods of from 5 to 24 hours.

The 1,2,3,4-tetrahydro-5-(phenylmethoxy)-2,3-naphthalenediol of formula II may be prepared from the corresponding triol IX

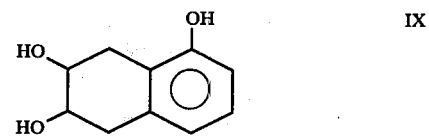

IX by first converting to the corresponding acetonide X

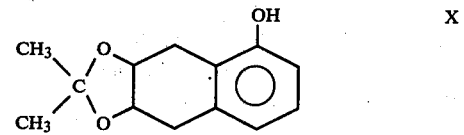

X as described in J. Med. Chem. 21, 913 (1978), where the OH groups are in the cis configuration (which is employed to make the compounds of formula I in the cis configuration). Thereafter, the acetonide X is converted to the corresponding benzyloxy derivative

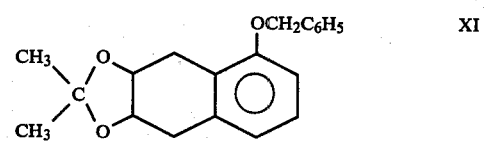

XI by reacting X with a benzylhalide in the presence of a weak base.

The benzyloxy derivative XI is then reacted with a weak acid, such as acetic acid to form the 1,2,3,4-tetrahydro-5-(phenylmethoxy)-2,3-naphthalenediol II.

Alternatively, 1,2,3,4-tetrahydro-5-(phenylmethoxy)-2,3-naphthalenediol II may be prepared by direct alkylation of triol IX with one equivalent of a base, such as sodium methoxide in a solvent, such as dimethylsulfoxide or dimethylformamide.

Compounds of formula I (where $R^3$ or $R^4$=H) may also be prepared by reacting 5-[3-alkylamino-2-hydroxypropoxy]-1,2,3,4-tetrahydro-2,3-naphthalenediol XII, J. Med. Chem. 21, 913 (1978) and U.S. Pat. No. 3,935,267 the disclosure of which is incorporated herein by reference (or any of its individual isomers which can be separated by standard chemical practice)

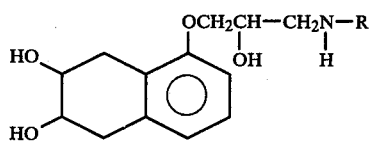

XII with an aromatic aldehyde, such as benzaldehyde in a hydrocarbon solvent, such as xylene or toluene at reflux for 1 to 3 days with continuous water separation to give the phenyl-oxazolidine protected intermediate XIII

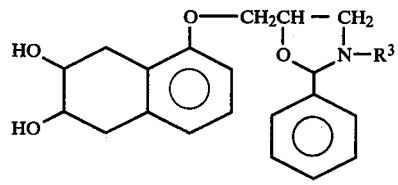

XIII

Alkylation of XIII with haloacetamides as previously described for the conversion of II to IV gives the alkylated intermediate XIV

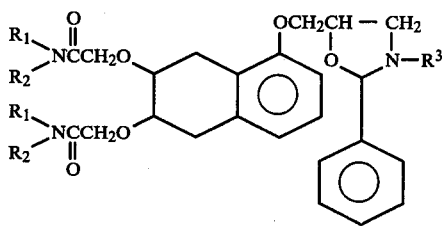

XIV

The Example XIV compounds represent novel intermediates.

Subsequent aqueous mineral acid hydrolysis removes the oxazolidinyl protecting group and gives compounds of formula I.

Thus, for example, a sample of 5-[3-[(1,1-dimethylethyl)amino]-2-hydroxypropoxy]-1,2,3,4-tetrahydro-2,3-cis-naphthalenediol, J. Med. Chem. 21, 913 (1978) and U.S. Pat. No. 3,935,267, may be fractionally crystallized from acetonitrile to give two racemates, R I and R II. Racemate R I, a 1:1 mixture of the 2S,3R,5S* and 2R,3S,5R* enantiomers,

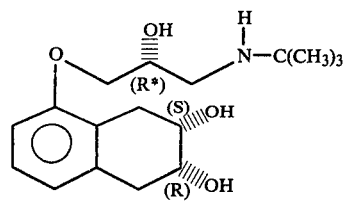

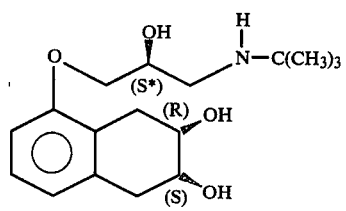

may be reacted with an aromatic aldehyde, such as benzaldehyde in a hydrocarbon solvent to give the phenyl-oxazolidine protected intermediate. Alkylation with haloacetamides, such as dipropylchloroacetamide, followed by removal of the phenyl-oxazolidinyl protecting group gives compounds of formula I as a 1:1 mixture of two enantiomers.

Alternatively, racemate R I may be converted to the salt of an optically active acid, such as dibenzoyl-1-tartaric acid, and fractionally crystallized to separate the enantiomeric salts. The separated enantiomeric salts can each be neutralized to give the individual enantiomers. Each enantiomer may then be reacted with an aromatic aldehyde as previously described to give the phenyl-oxazolidinyl protected intermediate. Alkylation with haloacetamides as previously described followed by removal of the phenyloxazolidinyl protecting group gives compounds of formula I as the individual enantiomer.

The compounds of formula I have antiarrhythmic activity as indicated by the Harris coronary-ligated dog test described by Harris, A. S., Circulation 1:1318–1328, 1950 (mentioned hereinbefore) and are useful in the treatment of arrhythmia in mammalian species, for example, rats and dogs.

A compound of formula I (above) as well as its physiologically acceptable acid salts or a compound of formula IV may be compounded according to pharmaceutical practice in oral or parenteral dosage forms, such as tablets, capsules, elixirs, injectables or powders for administration of about 10 mg to 2 gr per day, preferably 125 mg to 175 mg per day, in 2 to 4 divided doses.

The following Examples represent preferred embodiments of the present invention. All temperatures are expressed in degrees Centigrade.

EXAMPLE 1 cis-2,2'-[[1,2,3,4-Tetrahydro-5-(phenylmethoxy)2,3-naphthalenediyl]bis(oxy)]bis-[N,N-dipropylacetamide]

A. Acetonide of cis-5,6,7,8-tetrahydro 1,6,7-naphthalene-triol

A slurry of 5.4 g of cis-5,6,7,8-tetrahydro-1,6,7-naphthalene-triol in 50 ml of 2,2-dimethoxy propane is treated with 150 mg of TsOH (solution in 10 minutes). After 1 hour the solution is partitioned between ether and saturated bicarbonate solution. The organic layer is dried and evaporated to give 6.5 g essentially TLC homogeneous. Crystallization of a small sample from hexane/ethyl acetate gives material of m.p. 130.5°–131.5°.

B. cis-1,2,3,4-Tetrahydro-5-(phenylmethoxy)-2,3-naphthalenediol

A mixture of 10.66 g (0.0485 M) of the acetonide of cis-5,6,7,8-tetrahydro-1,6,7-naphthalenetriol and 2.7 g (0.05 M) of sodium methoxide is dissolved in 115 ml of dimethylsulfoxide, 50 ml of solvent removed in vacuo, a mixture of 5.64 (0.048 m) of benzyl chloride and 30 ml of dimethylsulfoxide added and the mixture stirred at room temperature overnight under nitrogen.

The solution is poured into a mixture of ether (500 ml), water (1 liter) and 10% aqueous sodium hydroxide (50 ml). The layers are separated, the aqueous layer extracted with ether (500 ml) and the combined ether extracts washed with water, saturated sodium chloride solution, dried and evaporated in vacuo to give 11.16 g of white solid (72%).

The 11.16 g of solid is dissolved in 100 ml of glacial acetic acid, 20 ml of water added and the mixture heated until a clear solution is obtained. The mixture is stirred at room temperature overnight. The mixture is filtered, the solid washed with glacial acetic acid and ether, and dried to give 8.2 g of white solid diol (84.6%).

C. cis-2,2'-[[1,2,3,4-Tetrahydro-5-(phenylmethoxy)-2,3-naphthalenediyl]bis(oxy)]bis-[N,N-dipropylacetamide]

An amount of 2 g of 50% sodium hydride-mineral oil dispersion is washed with hexane and then added portionwise over 15 minutes to a solution of 5.0 g (0.0185 M) of cis-1,2,3,4-tetrahydro-5-(phenylmethoxy)-2,3-naphthalenediol and 6.6 g (0.037 M) of N,N-di-n-propyl-α-chloroacetamide in 100 ml of dry dimethylsulfoxide. A 21° bath is used to maintain the mildly exothermic reaction below 28° C. The mixture is stirred a total of 4½ hours and then diluted with 5 ml of methanol. The mixture is diluted with water (500 ml) and extracted with ether (3×250 ml). The ether extract is washed (H$_2$O), dried (Na$_2$SO$_4$) and evaporated in vacuo to give 10.1 g of oil. Chromatography on 200 g of neutral Alumina III gives 0.3 g of forerun (eluted with 80 ml of 40% chloroform in hexane), 2.5 g of slightly impure product (eluted with 50 ml of 40% chloroform in hexane), and 7.7 g of product (eluted with 950 ml of 40–50% chloroform in hexane). The 2.5 g of impure material is re-chromatographed and the purified material combined with the 7.7 g obtained on the first column. This material is dried in vacuo at 140° C. to give the title compound as a very dense yellow oil, 8.3 g, with NMR and IR consistent with the desired product.

EXAMPLE 2 cis-2,2'-[(1,2,3,4-Tetrahydro-5-hydroxy-2,3-naphthalenediyl)bis(oxy)]bis-N,N-dipropylacetamide A solution of 4.4 g (0.008 M) of cis-2,2'-[[1,2,3,4-tetrahydro-5-(phenylmethoxy)-2,3-naphthalenediyl]bis-(oxy)]bis-[N,N-dipropylacetamide]prepared in Example 1 in 100 ml of absolute ethanol is placed in a Parr hydrogenator with 1 g of 5% palladium on carbon under 50 psi of hydrogen for 24 hours. The mixture is filtered and evaporated in vacuo to give a brown oil, 3.7 g. The oil is chromatographed on 80 g of neutral Alumina III to give 0.4 g of forerun (eluted with 110 ml chloroform) and 2.9 g of the desired product (eluted with ca. 500 ml of chloroform and 250 ml of 2% methanolic chloroform). The 2.9 g of product is dried in vacuo to give the title compound as a dense non-mobile yellow oil.

EXAMPLE 3 cis-2,2'-[[1,2,3,4-Tetrahydro-5-(oxiranyl-methoxy)-2,3-naphthalenediyl]bis(oxy)]bis-[N,N-dipropylacetamide]

A solution of 0.63 g (0.0158 M) of sodium hydroxide in 3.6 ml of water is added portionwise over 30 minutes to a gently refluxed solution of 7.3 g (0.0158 M) of cis-2,2'-[[1,2,3,4-tetrahydro-5-hydroxy-2,3-naphthalenediyl]bis(oxy)]bis-N,N-dipropylacetamide in 37 ml each of epichlorohydrin and acetone and 4.8 ml water. The resulting mixture is stirred vigorously and refluxed gently for 4.5 hours and then evaporated in vacuo. The residue is suspended in ether, washed (water and saturated sodium chloride solution), dried (Na$_2$SO$_4$), filtered and evaporated in vacuo to give an oil, 7.8 g. This material is chromatographed on 200 g of neutral Alumina III eluted with 1:1 hexane-chloroform to give 0.55 g of forerun and 4.6 g of the title compound as an oil, with NMR and IR consistent with the desired product.

EXAMPLE 4 cis-2,2'-[[5-[3-[(1,1-Dimethylethyl)amino]-2-hydroxypropoxy]-1,2,3,4-tetrahydro-2,3-naphthalenediyl]bis-(oxy)]bis[N,N-dipropylacetamide]

A solution of 1.5 g (0.0029 M) of cis-2,2'-[[1,2,3,4-tetrahydro-5-(oxiranyl-methoxy)-2,3-naphthalenediyl]bis-(oxy)]bis-[N,N-dipropylacetamide] in 5 ml of methanol and 20 ml of t-butylamine is stirred at room temperature overnight. The solution is evaporated in vacuo to give 1.7 g of oil. This material is dissolved in ether and extracted with 5% aqueous HCl. The aqueous layer is basified with aqueous NaOH and extracted with ether. The ether is washed (saturated NaCl solution), dried (Na$_2$SO$_4$), filtered and evaporated in vacuo to give the title compound as a dense oil, 1.52 g.

EXAMPLE 5 cis-4,4'-[[1,2,3,4-Tetrahydro-5-(phenylmethoxy)-2,3-naphthalenediyl]bis(oxyacetyl)]bis-[morpholine]

Following the procedure for the preparation of α-chloroacetamides described in JACS 78, 2556 (1956) a solution of 70.1 g (0.805 M) of morpholine in 300 ml of 1,2-dichloroethane is added to 200 ml of 20% aqueous sodium hydroxide and the mixture cooled in a −25° C. bath. Chloroacetyl chloride (111.6 g, 0.99 M) is added dropwise over 1 hour at a rate to keep reaction temperature at −20° to −10° C. The mixture is stirred for 1 hour at 0° C.±10 and then diluted with dichloroethane. The layers are separated and the aqueous layer is re-extracted with dichloroethane. The combined organic extract is washed (water, 5% aqueous hydrochloric acid, saturated sodium bicarbonate), dried (Na$_2$SO$_4$), filtered and the solvent removed in vacuo to give 54 g of oil. Vacuum distillation gives 46.4 g of the amide as a colorless liquid, bp 127.5°–128° C. @ 3.2 mm Hg.

An amount of 7.5 g of 50% sodium hydride-mineral oil dispersion is washed with hexane and then added over 45 minutes to a solution of 20.0 g (0.074 M) of cis-5,6,7,8-tetrahydro-1-benzoyloxy-6,7-naphthalenediol prepared as in Example 1, part B, and 22.2 g (0.148 M) of haloamide in 200 ml of dry dimethylsulfoxide. A cold water bath is used to maintain the reaction temperature below 26° C. The mixture is stirred at room temperature overnight under nitrogen. The mixture is diluted with 10 ml methanol, stirred 10 minutes and then 900 ml of water are added. The mixture is extracted with ether (800 ml) and then chloroform (1.5 l) to give a total of 30 g of crude product. Chromatography on 800 g of neutral Alumina III gives 1.25 g of forerun (800 ml chloroform), followed by 21.9 g of the desired product as an oil (1.5 l chloroform). Crystallization from 10% chloroform in ether gives the title compound as a white solid, m.p. 106°–110° C., 17.9 g.

EXAMPLE 6

2,2'-[(1,2,3,4-Tetrahydro-5-hydroxy-2,3-naphthalenediyl)bis(oxy)]bis[1-(4-morpholinyl)ethanone]

A mixture of 3.5 g of 5% palladium on carbon and 16.0 g (0.0305 M) of cis-4,4'-[[1,2,3,4-tetrahydro-5-(phenylmethoxy)-2,3-naphthalenediyl]bis(oxyacetyl)]-bis-[morpholine] in 150 ml absolute ethanol is placed on the Parr shaker under 50 psi of hydrogen at 60° C. for 20 hours. The mixture is filtered and evaporated in vacuo to give 13.1 g of product as a white foam. Chromatography on 250 g of neutral Alumina III gives 0.94 g of forerunproduct mixture (500 ml chloroform) and 10.6 g of product (900 ml of 0.2% methanolic chloroform) as a white amorphous solid. Analysis indicates 10% contamination with chloroform. An amount of 4.23 g of this solid is dried in vacuo at 165° C. to give the title compound as a yellow amorphous solid, 3.92 g, m.p. 68°–77° C.

EXAMPLE 7 cis-2,2'-[[1,2,3,4-Tetrahydro-5-(oxiranylmethoxy)-2,3-naphthalenediyl]bis(oxy)]bis[1-(4-morpholinyl)ethanone]

Following the procedure of Example 3, except substituting 2,2'-[(1,2,3,4-tetrahydro-5-hydroxy-2,3-naphthalenediyl)bis(oxy)]bis[1-(4-morpholinyl)ethanone] for cis-2,2'-[(1,2,3,4-tetrahydro-5-hydroxy-2,3-naphthalenediyl)bis(oxy)]bis-N,N-dipropylacetamide, the title compounds is obtained.

EXAMPLE 8 cis-2,2'-[[5-[3-[(1,1-Dimethylethyl)amino]-2-hydroxypropoxy]-1,2,3,4-tetrahydro-2,3-naphthalenediyl]bis(oxy)]bis[1-(4-morpholinyl)ethanone]

Following the procedure of Example 4, except substituting cis-2,2'-[[1,2,3,4-tetrahydro-5-(oxiranylmethoxy)-2,3-naphthalenediyl]bis(oxy)]-bis[1-(4-morpholinyl)ethanone] for cis-2,2'-[[1,2,3,4-tetrahydro-5-(oxiranylmethoxy)-2,3-naphthalenediyl]bis(oxy)]bis-[N,N-dipropylacetamide], the title compound is obtained.

EXAMPLES 9 TO 20

Following the procedure of Examples 1 and 2 except substituting for N,N-di-n-propyl-α-chloroacetamide the compound shown in Column I of Table A below, the 5-benzyloxy compound shown in Column II is obtained which is converted to the corresponding 5-hydroxy compound shown in Column III.

TABLE A

| Ex. No. | Column I | | | Column II | | Column III | |
|---|---|---|---|---|---|---|---|
| | $R^1$ | $R^2$ | X | $R^1$ | $R^2$ | $R^1$ | $R^2$ |
| 9. | H | $C_4H_9$ | Cl | as in Column I | | as in Column I | |
| 10. | H | H | Cl | | | | |
| 11. | $CH_3$ | H | Br | | | | |
| 12. | $CH_3$ | $CH_3$ | Cl | | | | |
| 13. | $C_2H_5$ | H | Cl | | | | |
| 14. | $C_3H_7$ | $C_3H_7$ | Br | | | | |
| 15. | $HOCH_2CH_2$ | $HOCH_2CH_2$ | Cl | | | | |
| 16. | $HO(CH_2)_2$ | H | Br | | | | |
| 17. | −N(aziridinyl) | | Cl | | | | |
| 18. | 4-methylpiperazinyl | | Cl | | | | |
| 19. | thiomorpholinyl | | Br | | | | |
| 20. | pyrrolidinyl | | Br | | | | |

EXAMPLES 21 TO 32

Following the procedure of Examples 3 and 4 except substituting for cis-2,2'-[(1,2,3,4-tetrahydro-5-hydroxy-2,3-naphthalenediyl)bis(oxy)]bis-[N,N-dipropylacetamide], the compounds shown in Column III of Table A, now shown in Column I of Table B below, and substituting for t-butylamine, the amine shown in Column II of Table B, the product shown in Column III is obtained.

B. trans-2,2'-[[1,2,3,4-Tetrahydro-5-(phenylmethoxy)-2,3-naphthalenediyl]bis(oxy)]bis-[N,N-dipropylacetamido]

Following the procedure of Example 1C except substituting 1,2,3,4-tetrahydro-5-(phenylmethoxy)-2,3-trans-naphthalenediol for cis-1,2,3,4-tetrahydro-5-(phenylmethoxy)-2,3-naphthalenediol, the title compound is formed.

EXAMPLE 34 trans-2,2'-[(1,2,3,4-Tetrahydro-5-hydroxy-2,3-naphthalenediyl)bis(oxy)]-bis-[N,N-dipropylacetamido]

TABLE B

| | Column I | | | Column II | | Column III | | | |
|---|---|---|---|---|---|---|---|---|---|
| Ex. No. | $R^1$ | $R^2$ | | $R^3$ | $R^4$ | $R^1$ | $R^2$ | $R^3$ | $R^4$ |
| 21. | H | $C_4H_9$ | | H | H | as in Column I | | as in Column II | |
| 22. | H | H | | $CH_3$ | $CH_3$ | | | | |
| 23. | $CH_3$ | H | | $CH_3$ | $C_2H_5$ | | | | |
| 24. | $CH_3$ | $CH_3$ | | $i\text{-}C_3H_7$ | H | | | | |
| 25. | $C_2H_5$ | H | | $n\text{-}C_4H_9$ | $n\text{-}C_4H_9$ | | | | |
| 26. | $C_3H_7$ | $C_3H_7$ | | H | H | | | | |
| 27. | $HOCH_2CH_2$ | $HOCH_2CH_2$ | | $C_2H_5$ | $CH_3$ | | | | |
| 28. | $HO(CH_2)_2$ | H | | H | $CH_3$ | | | | |
| 29. | -N(pyrrolidinyl) | | | $t\text{-}C_4H_9$ | $n\text{-}C_3H_7$ | | | | |
| 30. | -N(piperazinyl)NH | | | $n\text{-}C_3H_7$ | $n\text{-}C_3H_7$ | | | | |
| 31. | -N(thiomorpholinyl)S | | | H | H | | | | |
| 32. | -N(piperidinyl) | | | $CH_3$ | $n\text{-}C_4H_9$ | | | | |

EXAMPLE 33 trans-2,2'-[[1,2,3,4-Tetrahydro-5-(phenylmethoxy)-2,3-naphthalenediyl]-bis(oxy)]bis-[N,N-dipropylacetamide]

A. 1,2,3,4-Tetrahydro-5-(phenylmethoxy)-2,3-trans-naphthalenediol

An amount of 3.3 g (0.061 m) of sodium methoxide is added to a solution of 10.5 g (0.058 m) of trans-6,7-(5,6,7,8-tetrahydro)-1,6,7-naphthalene-triol in 100 ml dry dimethylsulfoxide and the mixture stirred at room temperature for 30 minutes. An amount of 9.9 g (0.058 m) of benzylbromide is added and the mixture stirred at room temperature for 5 hours. The mixture is diluted with 600 ml of water and extracted with chloroform. The chloroform extract is washed with 5% aqueous sodium hydroxide and saturated brine, dried ($Na_2SO_4$), filtered and evaporated in vacuo to give 13.3 g white solid (85%).

Following the procedure of Example 2 except substituting trans-2,2'-[[1,2,3,4-tetrahydro-5-(phenylmethoxy)-2,3-naphthalenediyl]bis(oxy)]bis-[N,N-dipropylacetamide] for cis-2,2'-[[1,2,3,4-tetrahydro-5-(phenylmethoxy)-2,3-naphthalenediyl]bis(oxy)]bis-[N,N-dipropylacetamide], the title compound is obtained.

EXAMPLE 35 cis-2,2'-[[5-[3-[(1,1-Dimethylethyl)amino]-2-hydroxypropoxy]-1,2,3,4-tetrahydro-2,3-naphthalene-diyl]bis-(oxy)]bis[N,N-dipropylacetamide]

A. 2,3-cis-1,2,3,4-Tetrahydro-5-[2,3-(epoxy)-propoxy]-2,3-naphthalenediol

A solution of 1.20 g (0.03 mole) of sodium methoxide and 5.4 g (0.03 mole) of cis-5,6,7,8-tetrahydro-1,6,7-naphthalenetriol in 200 ml of methanol is prepared under nitrogen. The residue obtained upon solvent removal is stirred overnight with 200 ml of dimethylsulfoxide and 4.65 g (0.05 mole) of epichlorohydrin under nitrogen. The bulk of the solvent is removed at 50° at 0.1 mm. and the residue dissolved in 500 ml of water. Extraction with chloroform (10×200 ml) gives 3.46 g of solid which is recrystallized from 150 ml of hexane-ethyl acetate to give 2.80 g of epoxy diol of the above title, m.p. 108°–111.5°.

B. cis-2,2'-[[1,2,3,4-Tetrahydro-5-(oxiranyl-methoxy)-2,3-naphthalenediyl]-bis(oxy)]bis-[N,N-dipropylacetamide]

An amount of 2.1 g of 50% sodium hydride-mineral oil dispersion is washed twice with hexane and then added to a solution of 5 g (0.021 m) of 2,3-cis-1,2,3,4-tetrahydro-5-[2,3-(epoxy)-propoxy]-2,3-naphthalenediol in 50 ml of dry dimethylsulfoxide. The mixture is stirred 20 minutes at room temperature and then 7.5 g (0.042 m) of α-chloro-N,N-dipropylacetamide is added (with a cold water bath used to prevent the reaction temperature from exceeding 30° C.). The mixture is stirred at room temperature for 4½ hours. The mixture is diluted with water and extracted with ether. The ether extract is washed with saturated brine, dried over sodium sulfate, filtered and the solvent removed in vacuo to give the crude product as an oil, 9.8 g. Chromatography on neutral Alumina III eluted with 1:1 hexane-chloroform gives the desired product as a dense oil, 6.5 g (60%).

C. cis-2,2'-[[5-[3-[(1,1-Dimethylethyl)amino]-2-hydroxypropoxy]-1,2,3,4-tetrahydro-2,3-naphthalenediyl]bis(oxy)]-bis[N,N-dipropylacetamide]

Following the procedure of Example 4, the title compound is obtained.

EXAMPLE 36 cis-2,2'-[[5-[3-[(1,1-Dimethylethyl)amino]-2-hydroxypropoxy]-1,2,3,4-tetrahydro-2,3-naphthalenediyl]bis-(oxy)]bis[N,N-dipropylacetamide]

A. 2,3-cis[[3-(1,1-Dimethylethyl)-2-phenyl-5-oxazolidinyl]methoxy]-1,2,3,4-tetrahydro-2,3-naphthalenediol An amount of 26.6 g (0.25 m) of benzaldehyde is added to a suspension of 15.5 g (0.05 m) of 2,3-cis-1,2,3,4-tetrahydro-5-[2-hydroxy-3-(1,1-dimethylethylamino)propoxy]-2,3-naphthalenediol prepared as described in U.S. Pat. No. 3,935,267 in 400 ml of xylene, and the mixture stirred at reflux for 48 hours with a Dean-Stark trap in the system. The solvent is removed in vacuo to give 20 g of dense oil residue. The material is chromatographed on 300 g of neutral Alumina III to give 1.1 g of forerun (benzaldehyde) eluted with benzene; and 10.5 g (0.026 m) of the desired benzylidine product eluted with 50–100% chloroform-benzene (3.31) and 5% methanol-chloroform (1 l.). The 10.5 g (52.7%) of benzylidene product (title compound) could not be crystallized and is used in the next step without further purification.

B. 2,2'-[[5-[[3-(1,1-Dimethylethyl)-2-phenyl-5-oxazolidinyl]methoxy]-1,2,3,4-tetrahydro-2,3-naphthalenediyl]bis(oxy)]bis[N,N-dipropylacetamide]

An amount of 2.4 g of 50% sodium hydride-mineral oil dispersion is washed with hexane and then added portionwise over 10 minutes to a solution of 8.95 g (0.0225 m) of 2,3-cis[[3-(1,1-dimethylethyl)-2-phenyl-5-oxazolidinyl]methoxy]-1,2,3,4-tetrahydro-2,3-naphthalenediol in 150 ml of dry dimethylsulfoxide. The mixture is stirred 30 minutes at room temperature under nitrogen. An amount of 8.0 g (0.045 m) of α-chloro-N,N-dipropylacetamide is added portionwise over 20 minutes at a rate to keep the reaction temperature below 27° C. (22° C. bath). The mixture is stirred 5 hours at room temperature and then diluted with 10 ml methanol followed by 700 ml water. The mixture is extracted with ether (4×250 ml). The ether extract is washed with water and saturated brine, dried (Na₂SO₄), filtered and evaporated in vacuo to give the bis-alkylated title product as a dense oil, 13.8 g (90%).

C. cis-2,2'-[[5-[3-[(1,1-Dimethylethyl)amino]-2-hydroxypropoxy]-1,2,3,4-tetrahydro-2,3-naphthalenediyl]bis(oxy)]bis[N,N-dipropylacetamide]

13.8 g of 2,2'-[[5-[[3-(1,1-dimethylethyl)-2-phenyl-5-oxazolidinyl]methoxy]-1,2,3,4-tetrahydro-2,3-naphthalenediyl]bis(oxy)]bis[N,N-dipropylacetamide] is suspended in 50 ml of 1 N aqueous hydrochloric acid and warmed gently on the steam bath for 45 minutes. The mixture is diluted with 100 ml of water and washed with ether. The acidic aqueous layer is then basified and extracted with ether (3×300 ml). The ether extract is washed with saturated brine, dried (Na₂SO₄), filtered and evaporated in vacuo to give a dense oil, 10.7 g. Chromatography on 275 g of neutral Alumina gives 1.08 g of forerun (370 ml of 25% hexane in chloroform) followed by 8.4 g of slightly contaminated product (1.9 l of 25–100% hexane in chloroform and 1.6 l of chloroform). The 8.4 g is rechromatographed on Alumina eluted with methanol in ethyl acetate to give 7.9 g of product. Further purification by acid-base extraction gives cis-2,2'-[[5-[3-[(1,1-dimethylethyl)amino]-2-hydroxypropoxy]-1,2,3,4-tetrahydro-2,3-naphthalenediyl]bis(oxy)]bis[N,N-dipropylacetamide] as a dense oil, 4.79 g (0.008 m) 39.9%.

EXAMPLES 37 to 48

Following the procedure of Example 36 except substituting for 2,3-cis-1,2,3,4-tetrahydro-5-[2-hydroxy-3-(1,1-dimethylethylamino)propoxy]-2,3-naphthalenediol the compound shown in Column I of Table C below and substituting for N,N-di-n-propyl-α-chloroacetamide, the compound shown in Column II, the product shown in Column III is obtained.

TABLE C

| | Column I | | Column II | | | Column III | | | |
|---|---|---|---|---|---|---|---|---|---|
| Ex. No. | $R^3$ | $R^4$ | $R^1$ | $R^2$ | X | $R^1$ | $R^2$ | $R^3$ | $R^4$ |
| 37. | H | H | $CH_3CH_2CH=CH-$ | $C_4H_9$ | Cl | as in Column II | | s in Column I | |
| 38. | H | $CH_3$ | $HOCH_2$ | H | Cl | | | | |
| 39. | H | $C_2H_5$ | $HO(CH_2)_3-$ | H | Br | | | | |
| 40. | H | $CH_3$ | $C_2H_5$ | $CH_3$ | Cl | | | | |
| 41. | H | $n-C_4H_9$ | $CH_2=CHCH_2$ | H | Cl | | | | |
| 42. | H | H | $CH_3CH=CHCH_2-$ | $CH_3CH=CHCH_2-$ | Br | | | | |
| 43. | H | H | $HO(CH_2)_2-$ | $HO(CH_2)_2$ | Cl | | | | |
| 44. | H | $CH_3$ | $HO(CH_2)_2$ | H | Br | | | | |
| 45. | H | H | $-N\underset{}{\diagdown}$ (pyrrolidinyl) | | Cl | | | | |
| 46. | $CH_3$ | H | $CH_3N\diagdown N-$ (N-methylpiperazinyl) | | Cl | | | | |
| 47. | H | $C_2H_5$ | $-N\diagdown S$ (thiomorpholinyl) | | Br | | | | |
| 48. | H | H | $-N\diagdown$ (piperidinyl) | | Br | | | | |

It will be appreciated that the compounds of Examples 37 to 48 may comprise cis or trans isomers depending upon the isomeric configuration of the starting compounds shown in Column I.

EXAMPLE 49

[2R-[2α,3α,5(R*)]]-2,2'-[[5-[3-[(1,1-Dimethylethyl)-amino]-2-hydroxypropoxy]-1,2,3,4-tetrahydro-2,3-naphthalenediyl]bis(oxy)]bis[N,N-dipropylacetamide]

A. [2R-[2α,3α,5(R*)]]-5-[(2,2-Dimethyl-1,3-dioxolan-4-yl)methoxy]-1,2,3,4-tetrahydro-2,3-naphthalenediol and [2S-[2α,3α,5(R*)]]-5-[(2,2-Dimethyl-1,3-dioxolan-4-yl)methoxy]-1,2,3,4-tetrahydro-2,3-naphthalenediol To a solution of cis-5,6,7,8-tetrahydro-1,6,7-naphthalenetriol (21.6 g, 0.12 mol) in dimethylformamide (200 ml) at 23° is added 6.04 g sodium hydride 50% oil dispersion (after prior washing with hexane 50 ml) and 15 minutes after cessation of gas evolution, (R)-tosylsolketal (that is, (R)-2,2-dimethyl-1,3-dioxolane-4-methanol, 4-methylbenzenesulfonate ester prepared as described by J. J. Baldwin, et al., J. Org. Chem., 43, (25 4876 (1978)) (34.2 g, 0.12 mol) is added all at once and rinsed in with dimethylformamide (50 ml). The reaction mixture is stirred under argon and heated to and maintained at 65° C. for 26 hours.

The mixture is cooled to 23°, diluted with methanol (20 ml) and concentrated at 55° C., 1 mm Hg, to a dark brown semi-solid. The residue is taken up in chloroform (0.7 l), extracted with brine (0.3 l), water (1 l.) and saturated $NaHCO_3$ solution. Each of the aqueous layers is reextracted with $CHCl_3$ (1 l.) and the combined organic layers are dried over $K_2CO_3$, filtered and evaporated to give a dark tan semi-solid residue. The residue is then triturated with ether (1 l.) and the resulting crystals removed by filtration. They are washed with several 50 ml portions of ether until the color remains unchanged and then with 50 ml of cold methanol. This treatment gives nearly colorless product largely free of the second diasteriomer. Recrystallization from 450 ml of hot chloroform then affords 31.9 g (46%) of pure product, m.p. 149°-150°, $[\alpha]_D^{22}=-2.08°$ (c=1.70, methanol).

B. [2R-[2α,3α,5(R*)]]-2,2'-[[5-[(2,2-Dimethyl-1,3-dioxolan-4-yl)methoxy]-1,2,3,4-tetrahydro-2,3-naphthalenediyl]-bis(oxy)]bis[N,N-dipropylacetamide]

To a solution of [2R-[2α,3α,5(R*)]]-5-[(2,2-dimethyl-1,3-dioxolan-4-yl)methoxy-1,2,3,4-tetrahydro-2,3-naphthalenediol (8.23 g, 0.028 mol) and N,N-di-n-propyl-chloroacetamide (10.3 g, 0.058 mol) in dry dimethylsulfoxide (150 ml) is added 50% oil dispersion of sodium hydride (2.78 g, 0.058 mol) after washing with hexane, and the suspension is allowed to stir at 22° for 18 hours under argon at room temperature. To the resulting deep tan solution is added methanol (10 ml) and the solution is poured into water (800 ml) and extracted with ether (2×600 ml). The organic layer is reextracted with brine (300 ml) and dried over potassium carbonate, filtered and evaporated to a tan crystalline mass (16.2 g). The material is dissolved in a minimum volume of boiling isopropyl ether and allowed to stand to give after hexane washing, air drying and vacuum drying (2 mm, 60°, 2 hours) 13.35 g of the title compound (V) as colorless rosettes of needles, m.p. 77°–78°, $\alpha_D = +1.0°$ (c=2, MeOH). $R_f = 0.35$, $SiO_2$, 0.5% MeOH/CHCl$_3$.

C. [2R-[2α,3α,5(R*)]]-2,2'-[[5-(2,3-Dihydroxypropoxy)-1,2,3,4-tetrahydro-2,3-naphthalenediyl]bis-(oxy)]bis[N,N-dipropylacetamide]

To a slurry of [2R-[2α,3α,5(R*)]]-2,2'-[[5-[(2,2-dimethyl-1,3-dioxolan-4-yl)methoxy]1,2,3,4-tetrahydro-2,3-naphthalenediyl]bis(oxy)]bis[N,N-dipropylacetamide] (12.5 g, 0.022 mol) in water (30 ml) is added acetone (20 ml) and absolute ethanol (50 ml) and 5% aqueous hydrochloric acid (70 ml) and the mixture is heated on a steam bath for 30 minutes with aliquots of absolute ethanol added as required to maintain a clear solution. The mixture is cooled to room temperature, diluted with benzene (500 ml) and concentrated to a dense oil. The resulting oil is partitioned between brine and chloroform and the organic layer is dried over $K_2CO_3$, filtered and evaporated to yield a dense oil. Drying at 0.5 mm Hg vacuum at 45° C. for 2 hours affords the title compound as a dense oil, 11.9 g (some CHCl$_3$ remains) $\alpha_D = -8.1°$ (c=4, MeOH). $R_f$—0.15, $SiO_2$, 0.5% MeOH/CHCl$_3$. Yield 95%.

D. [2R-[2α,3α,5(R*)]]-2,2'-[[1,2,3,4-Tetrahydro-5-[2-hydroxy-3-[[(2,4,6-trimethylphenyl)sulfonyl]oxy]propoxy]-2,3-naphthalenediyl]bis(oxy)]bis[N,N-dipropylacetamide]

To a stirred solution of [2R-[2α,3α,5(R*)]]-2,2'-[[5-(2,3-dihydroxypropoxy)-1,2,3,4-tetrahydro-2,3-naphthalenediyl]bis(oxy)]bis[N,N-dipropylacetamide] (11 g, 0.0205 mol) in pyridine (50 ml) and chloroform (70 ml) at −30° C. under argon is added mesitylenesulfonyl chloride (4.5 g, 0.0206 mol) as a finely ground powder, portionwise over 15 minutes and the resulting light yellow solution is stored in a freezer (−15° C.) overnight. The clear yellow solution is poured onto a mixture of ice and saturated solution of ammonium sulfate and is extracted with ether (2×500 ml). The ether layer is repeatedly extracted with saturated aqueous solution of cupric sulfate until there is no further color changes. The organic layer is dried over $Na_2SO_4$, filtered and concentrated to give 13.2 g of light yellow oil. The oil is dried at 0.5 mm Hg/50° for 1 hour to yield a dense oil 12.2 g. TLC reveals trace impurities of unreacted starting material, tlc purity of major product ≧93% of the title compound VII, $\alpha_D = +0.4°$ (c=4, MeOH). The product is used without further purification. Yield 83% $R_f = 0.4$, $SiO_2$, 0.5% MeOH/CHCl$_3$.

E.
[2R-[2α,3α,5(R*)]]-2,2'-[[5-[3-[(1,1-Dimethylethyl)amino]-2-hydroxypropoxy]-1,2,3,4-tetrahydro-2,3-naphthalenediyl]-bis(oxy)]bis[N,N-dipropylacetamide]- (Isomer B)

A stirred solution of [2R-[2α,3α,5(R*)]]-2,2'-[[1,2,3,4-tetrahydro-5-[2-hydroxy-3-[[(2,4,6-trimethylphenyl)sulfonyl]oxy]propoxy]-2,3-naphthalenediyl]bis(oxy)]-bis[N,N-dipropylacetamide] in 150 ml of tert-butylamine is stirred in a 1 l. pressure vessel for 18 hours. The light orange solution is treated with hexane (50 ml) and after standing 20 minutes the solution is filtered and concentrated to dryness. The dense oil is taken up in ether and partitioned with brine and then 5% aqueous hydrochloric acid. The acidic layer is made alkaline to pH=9 with aqueous KOH (25%) with ice cooling and partitioned with ether (2×600 ml), the ether layer dried over MgSO$_4$, filtered and evaporated to a dense oil which, after vacuum (0.5 mm) drying at 70° for 20 minutes gives 34.2 g of a glassy viscous oil. This material is chromatographed on 700 g of alumina (act III) in a 70 mm column. A 96:4 ether/methanol mixture removes the two impurities of $R_f$ 0.74 and 0.63 ($Al_2O_3$—10% methanol in ether) and 10% methanol in ether removes the pure product. After rechromatographing the mixed fractions, drying the eluted solutions (anhydrous $K_2CO_3$) and concentration a total of 24.37 g (60%) of product is obtained. This is then dried at 160° at 0.06 mm for 2 hours, $R_f$ 0.17 ($Al_2O_3$—10% methanol in ether). $\alpha_D = -6.1°$ (c32 2, MeOH) TLC, $R_f$ 0.35, 2% MeOH in CHCl$_3$ on $Al_2O_3$ plates.

Analysis calc'd for $C_{33}H_{57}N_3O_6$: C, 66.97; H, 9.71; N, 7.10. Found: C, 66.65; H, 9.72; N, 7.20.

EXAMPLE 50 cis-2,2'-[[5-[3-[(1,1-Dimethylethyl)amino]-2-hydroxypropoxy]-1,2,3,4-tetrahydro-2,3-naphthalene-diyl]bis-(oxy)bis[N,N-dipropylacetamide], a 1:1 mixture of the 2S,3R,5S* and 2R,3S,5R* enantiomers A. [2S,3R,5S*] and [2R,3S,5R*]-5-[3-[(1,1-Dimethylethyl)amino]-2-hydroxy-propoxy]-1,2,3,4-tetrahydro-2,3-cis-naphthalenediol An amount of 48 g of 5-[3-[(1,1-dimethyl-ethyl)amino]-2-hydroxypropoxy]-1,2,3,4-tetrahydro-2,3-cis-naphthalenediol, a mixture of four enantiomers, is suspended in 800 ml of acetonitrile, warmed to 60° C. and filtered. The filtrate is let stand at room temperature and after 3 hours three crops of crystalline product are isolated to give 20.4 g, m.p. 130°–136° C. Two recrystallizations from acetonitrile gives the title compounds, 11.06 g, m.p. 137°–139° C., a 1:1 mixture of two enantiomers.

B. [2S,3R,5S*] and [2R,3S,5R*]-2,3-cis-[[3-(1,1-dimethylethyl)-2-phenyl-5-oxazolidinyl]methoxy]-1,2,3,4-tetrahydro-2,3-naphthalenediol A mixture of 11 g of a 1:1 mixture of [2S,3R,5S*] and [2R,3S,5R*]-5-[3-[(1,1-dimethylethyl)amino]-2-hydroxypropoxy]-1,2,3,4-tetrahydro-2,3-cis-naphthalenediol and 18.8 g of benzaldehyde in 220 ml of xylene is stirred at reflux for 29 hours with a water separator. The mixture is evaporated in vacuo and the residue is triturated with 50 ml of hot isopropylether and let stand at room temperature to crystallize. The crystalline product is collected and recrystallized twice from benzene to give the title compound, 9.1 g m.p. 124°–134° C., 64%. Hydrolysis of a small sample gives recovered starting material as the same 1:1 mixture of enantiomers.

C. cis-2,2'-[[5-[3-[(1,1-Dimethylethyl)-amino]-2-hydroxypropoxy]-1,2,3,4-tetrahydro-2,3-naphthalenediyl]bis(oxy)-bis[N,N-dipropylacetamide], a 1:1 mixture of the 2S,3R,5S* and 2R,3S,5R* enantiomers An amount of 2.4 g of 50% sodium hydride-mineral oil dispersion is washed with hexane and then added portionwise over 10 minutes to a solution of 8.95 g of [2S,3R,5S*] and [2R,3S,5R*]2,3-cis[3-(1,1-dimethylethyl)-2-phenyl-5-oxazolidinyl]methoxy]-1,2,3,4-tetrahydro-2,3-naphthalenediol in 150 ml of dry dimethylsulfoxide. The mixture is stirred 30 minutes at room temperature under nitrogen. An amount of 8 g of α-chloro-N,N-dipropylacetamide is added portionwise over 20 minutes at a rate to keep the reaction temperature below 27° C. The mixture is stirred 5 hours at room temperature and then diluted with 10 ml methanol followed by 700 ml of water. The mixture is extracted with ether (4×250 ml). The ether extract is washed with water and saturated brine, dried over sodium sulfate, filtered, and the solvent removed in vacuo to give the bis-alkylated product as a dense oil, 13.8 g (90%). This material is suspended in 50 ml of 1 N hydrochloric acid and warmed gently on the steam bath for 45 minutes. The mixture is diluted with water (100 ml) and washed with ether. The aqueous layer is then diluted with 50 ml of 10% aqueous sodium hydroxide and extracted with ether (3×300 ml). The ether extract is washed with saturated brine, dried over sodium sulfate, filtered, and the filtrate is evaporated in vacuo to give a dense oil 10.7 g. Chromatography on neutral Alumina III gives 7.9 g of product. Further purification by acid-base extraction gives the title compound as a dense oil, 4.79 g (40%).

EXAMPLE 51

[2R-[2α,3α,5(R*)]]-2,2'-[[5-[3-[(1,1-Dimethylethyl)-amino]-2-hydroxypropoxy]-1,2,3,4-tetrahydro-2,3-naphthalenediyl]bis(oxy)]bis[N,N-dipropylacetamide]

A. [2R-[2α,3α,5(R*)]]-5-[[3-(1,1-Dimethylethyl)-2-phenyl-5-oxazolidinyl]methoxy]1,2,3,4-tetrahydro-2,3-cis-naphthalenediol A mixture of 8 g of [2R-[2α,3α,5(R*)]]-5-[3-[(1,1-dimethylethyl)amino]-2-hydroxypropoxy]1,2,3,4-tetrahydro-2,3-naphthalenediol and 13.7 g of benzaldehyde in 200 ml of xylene is stirred at reflux for 30 hours with a water separator. The mixture is evaporated in vacuo and the residue triturated with isopropylether and let stand at room temperature to crystallize. The crystalline product is collected and recrystallized from benzene to give the title compound 7.7 g, 75%.

B. [2R-[2α,3α,5(R*)]]-2,2'-[[5-[3-[(1,1-Dimethylethyl)amino]-2-hydroxypropoxy]1,2,3,4-tetrahydro-2,3-naphthalenediyl]bis(oxy)]bis[N,N-dipropylacetamide]

An amount of 1.9 g of 50% sodium hydride-mineral oil dispersion is washed with hexane and added portionwise over 10 minutes to a solution of 7.7 g of [2R-[2α,3α,5(R*)]]-5-[[3-(1,1-dimethyl-ethyl)-2-phenyl-5-oxazolidinyl]methoxy]-1,2,3,4-tetrahydro-2,3-cis-naphthalenediol in 125 ml of dry dimethylsulfoxide. The mixture is stirred 30 minutes at room temperature under nitrogen. An amount of 6.9 g of α-chloro-N,N-dipropylacetamide is added portionwise over 20 minutes. The mixture is stirred 5 hours at room temperature and then diluted with 10 ml of methanol followed by 600 ml of water. The mixture is extracted with ether (4×250 ml). The ether extract is washed with water and saturated brine, dried over sodium sulfate and filtered. The solvent is removed in vacuo to give the bis alkylated product as a dense oil, 11.9 g.

The 11.9 g of oil is suspended in 50 ml of 1 N hydrochloric acid and warmed gently on the steam bath for 1 hour. The mixture is diluted with 100 ml of water and washed with ether. The aqueous solution is diluted with 50 ml of 10% aqueous sodium hydroxide and extracted with ether (4×250 ml). The ether extract is washed with saturated brine, dried over sodium sulfate, filtered, and the solvent removed in vacuo to give a dense oil. The oil is chromatographed on neutral Alumina III (eluted with 25 to 0% hexane in chloroform) to give the product as a dense oil, 7.5 g. Further purification by acid-base extraction gives the title compound as a dense yellow oil, 6.5 g, 56%, $[\alpha]_D = -6.1°$ (c=3 MeOH).

What is claimed is:

1. A compound having the structure

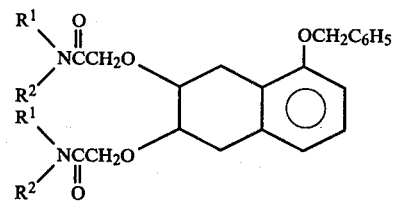

wherein $R^1$ and $R^2$ are the same or different and are hydrogen, lower alkyl, lower alkenyl or hydroxy-lower alkyl, or $R^1$ and $R^2$ are taken together with the nitrogen atom to which they are attached to form a 5- to 7-membered heterocyclic ring containing one or two heteroatoms, and which may contain in addition to said nitrogen atom, one nitrogen, oxygen or sulfur atom.

2. The compound as defined in claim 1 wherein $R^1$ and $R^2$ are each lower alkyl.

3. The compound as defined in claim 1 wherein $R^1$ and $R^2$ are each n-propyl.

4. The compound as defined in claim 1 wherein

is morpholino.

5. A compound having the structure

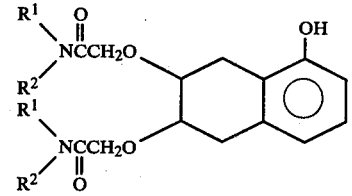

wherein $R^1$ and $R^2$ are the same or different and are hydrogen, lower alkyl, lower alkenyl or hydroxy-lower alkyl, or $R^1$ and $R^2$ are taken together with the nitrogen atom to which they are attached to form a 5- or 7-membered heterocyclic ring containing one or two heteroatoms, and which may contain in addition to said nitrogen atom, one nitrogen, oxygen or sulfur atom.

6. The compound as defined in claim 5 wherein $R^1$ and $R^2$ are each n-propyl.

7. The compound as defined in claim 5 wherein

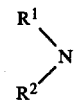

is morpholino.

8. A compound having the structure

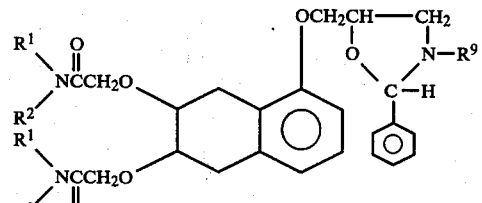

wherein $R^1$ and $R^2$ are the same or different and are hydrogen, lower alkyl, lower alkenyl or hydroxy-lower alkyl, or $R^1$ and $R^2$ are taken together with the nitrogen atom to which they are attached to form a 5- or 7-membered heterocyclic ring containing one or two heteroatoms, and which may contain in addition to said nitrogen atom, one nitrogen, oxygen or sulfur atom, and $R^3$ is lower alkyl.

* * * * *

UNITED STATES PATENT AND TRADEMARK OFFICE
CERTIFICATE OF CORRECTION

PATENT NO. : 4,350,812

DATED : September 21, 1982

INVENTOR(S) : Frederic P. Hauck et al.

It is certified that error appears in the above—identified patent and that said Letters Patent is hereby corrected as shown below:

On the abstract page, the second and third structures should read, respectively,

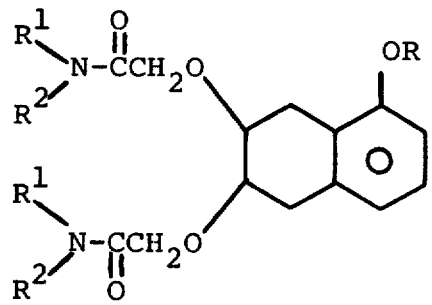 ; 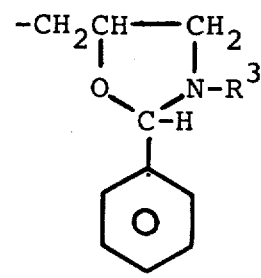

Column 5, line 36, "infraction" should read --infarction--.
Column 12, line 11, "compounds" should read --compound--.
Column 11, Table A, Ex. 17-20, the headings in Col. I should read -- 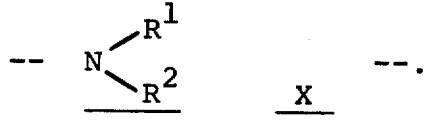 --.

Column 13, Table B, Ex. 29-32, the heading in Column I should read

-- 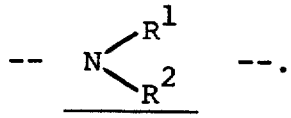 --.

Column 14, line 21, "dipropylacetamido" should read --dipropylacetamide--.

Columns 17 and 18, Table C, Ex. 45-48, the heading of the first column of structures should read --$\underline{R^3}$--; the heading of the second column of structures should read --$\underline{R^4}$--; the heading of the third column of structures should read

UNITED STATES PATENT AND TRADEMARK OFFICE
CERTIFICATE OF CORRECTION

PATENT NO. : 4,350,812  
DATED : September 21, 1982  
INVENTOR(S) : Frederic P. Hauck et al.

It is certified that error appears in the above—identified patent and that said Letters Patent is hereby corrected as shown below:

$--N\begin{matrix}R^1\\R^2\end{matrix}--$; and the heading of the fourth column of structures should read --$\underline{X}$--.

Column 20, line 14, "c32 2" should read --c=2--.

Signed and Sealed this

First Day of February 1983

[SEAL]

Attest:

Attesting Officer

GERALD J. MOSSINGHOFF

Commissioner of Patents and Trademarks